(12) United States Patent
Kroll et al.

(10) Patent No.: US 7,751,887 B1
(45) Date of Patent: **\*Jul. 6, 2010**

(54) TIERED ANTITACHYCARDIA PACING AND PRE-PULSING THERAPY

(75) Inventors: Mark W. Kroll, Crystal Bay, MN (US); Michael Benser, Valencia, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 11/413,773

(22) Filed: Apr. 28, 2006

(51) Int. Cl.
*A61N 1/368* (2006.01)

(52) U.S. Cl. ...................................................... 607/14

(58) Field of Classification Search ............... 607/4, 607/9, 14, 15
See application file for complete search history.

(56) References Cited

U.S. PATENT DOCUMENTS

| | | | | |
|---|---|---|---|---|
| 4,830,006 | A * | 5/1989 | Haluska et al. ............... | 607/4 |
| 5,243,978 | A | 9/1993 | Duffin, Jr. .................... | 607/11 |
| 5,330,509 | A | 7/1994 | Kroll et al. ................... | 607/14 |
| 5,466,254 | A | 11/1995 | Helland ........................ | 607/123 |
| 5,674,251 | A | 10/1997 | Combs et al. ................. | 607/4 |
| 6,473,645 | B1 | 10/2002 | Levine .......................... | 607/9 |
| 6,606,516 | B2 | 8/2003 | Levine .......................... | 607/9 |
| 6,711,442 | B1 | 3/2004 | Swerdlow et al. ............ | 607/63 |
| 6,731,982 | B1 | 5/2004 | Kroll et al. ................... | 607/14 |
| 6,748,268 | B1 | 6/2004 | Helland et al. ................ | 607/4 |
| 6,754,525 | B1 | 6/2004 | Province et al. ............... | 607/4 |
| 6,795,731 | B1 | 9/2004 | Kroll et al. | |
| 7,158,826 | B1 | 1/2007 | Kroll et al. | |
| 7,231,255 | B1 | 6/2007 | Kroll et al. | |
| 7,596,410 | B1 * | 9/2009 | Kroll et al. ................... | 607/14 |
| 2002/0082658 | A1 | 6/2002 | Heinrich et al. | |
| 2002/0193834 | A1 | 12/2002 | Levine .......................... | 607/9 |
| 2003/0050681 | A1 | 3/2003 | Pianca et al. ................. | 607/125 |
| 2004/0167579 | A1 * | 8/2004 | Sharma et al. ................ | 607/14 |
| 2004/0176809 | A1 * | 9/2004 | Cho et al. ...................... | 607/14 |
| 2005/0049644 | A1 | 3/2005 | Warren et al. ................. | 607/9 |
| 2005/0070966 | A1 * | 3/2005 | Sharma ......................... | 607/14 |
| 2006/0122649 | A1 | 6/2006 | Ghanem et al. | |

FOREIGN PATENT DOCUMENTS

| | | |
|---|---|---|
| EP | 1 249 254 A2 | 10/2002 |
| EP | 1 304 137 A2 | 4/2003 |
| EP | 1 249 254 A3 | 3/2004 |

OTHER PUBLICATIONS

NonFinal Office Action, mailed Apr. 15, 2009: Related U.S. Appl. No. 11/413,772.

* cited by examiner

*Primary Examiner*—Kennedy J Schaetzle
*Assistant Examiner*—Jessica Sarcione

(57) ABSTRACT

An implantable system applies tiered antitachycardia pacing (ATP) that may be combined with pre-pulsing therapy in order to reduce pain. In one implementation, an exemplary system applies a progression of increasingly potent pacing vectors, progressing in an initial tier from small electrodes inside the heart to later tiers that increasingly use a large electrode surface outside the heart. In the latter tiers, a pre-pulse may be added prior to each ATP pulse to reduce the sensation of pain.

13 Claims, 13 Drawing Sheets

TIERED ANTITACHYCARDIA PACING AND PRE-PULSING THERAPY

TECHNICAL FIELD

Subject matter presented herein relates generally to implantable medical devices and more particularly to tiered antitachycardia pacing and pre-pulsing therapy.

BACKGROUND

Abnormally fast heart rates are called tachycardias and pose the danger of progressing into ventricular fibrillation, which can be fatal. As used herein, the term "tachycardia" thus refers to a heart rate that is abnormally high or to an arrhythmia that includes a fast heart rate that is too high and potentially dangerous if permitted to continue.

When the ventricular chambers beat too quickly, the arrhythmia is referred to as ventricular tachycardia (known as VT). During ventricular tachycardia, the ventricles typically do not fill properly, and do not pump enough blood to the body. Symptoms of ventricular tachycardia include faintness, pounding in the chest, and loss of consciousness. These tachycardias may result from a number of different causes. For example, patients who have had myocardial infarctions, or other diseases that create scarring in the ventricular region of the heart, often develop monomorphic ventricular tachycardias, a type of tachycardia that originates from one ventricular focus, for example, from an area of scarring on the heart. This type of tachycardia is typically uniform and occurs at a regular rate. Faster instances of monomorphic ventricular tachycardias are often associated with hemodynamic compromise, whereas slower instances can be very stable.

When cells die in a myocardial infarct, they electrically uncouple from neighboring viable cells, making the infarct completely inexcitable. Intrinsic or paced wavefronts encountering such an obstacle generally split into two components that collide and recombine on the opposite side of the infarct. When tissue adjacent to the infarct excites prematurely, however, reentry can result if one of the wavefronts gets blocked in a region with reduced excitability. When blocking of one wavefront occurs, the other wavefront may be able to reenter the initial block site, causing a "reentrant circuit." Action potentials will continually propagate around the infarct at a rate considerably faster than the heart's intrinsic rate—i.e., ventricular tachycardia. The reentrant circuit can be thought of as a conduction wavefront propagating along a tissue mass of approximately circular geometry.

This circular conduction will consist of a portion of refractory tissue and a portion of excitable tissue. To terminate the circuit, a pacing stimulus should be provided at the time and location when the tissue just comes out of refractoriness. If this occurs, the paced stimulation wavefront proceeds toward the advancing wavefront of the circuit, colliding with the wavefront and interrupting the circuit. Accordingly, the probability of antitachycardia pacing succeeding in terminating the ventricular tachycardia is related to the ability of the pacing stimulation wavefront to arrive at the location of the reentrant circuit (e.g., within a myocardium) in such a manner that the reentrant circuit is modified or interrupted.

There are several different pacing modalities that have been suggested for termination of tachycardia. The underlying principle is that if a pacing pulse stimulates the heart at least once shortly after a heartbeat, before the next naturally occurring heartbeat of tachycardic rate, the heart may successively revert to sinus rhythm.

Ventricular tachycardia is sometimes controlled by an implanted cardiac device that applies electrical therapies. For example, an implantable cardioverter-defibrillator (ICD) applies antitachycardia pacing (ATP) or an electric shock to the heart muscle after which a normal sinus rhythm often ensues. If an electric shock (i.e., cardioversion) is used to treat the ventricular tachycardia because the ventricular tachycardia has become recalcitrant, the electric shock may be in the form of specially timed pacemaker pulses (unfelt by the patient) or by high voltage shock. High voltage shocks, if required, are usually painful to the patient.

So, even though ATP is used to convert ventricular tachycardias into normal sinus rhythm, conventional ATP is not always completely successful at returning the heart to normal sinus rhythm. Consequently, cardioversion is used, but cardioversion is usually painful or at least unpleasant. Additionally, conventional ATP sometimes accelerates the rhythm to ventricular fibrillation. In women, for example, acceleration from ATP can occur in approximately 15% of ATP attempts. Thus, improved methods for increasing the success rate of ATP, for decreasing the time needed to convert the ventricular tachycardia to a normal sinus rhythm, and for reducing pain, are needed.

SUMMARY

An implantable system applies tiered antitachycardia pacing (ATP) which, in some embodiments, is combined with pre-pulsing therapy in order to reduce pain. In one implementation, an exemplary system applies a progression of increasingly potent pacing vectors, progressing in an initial tier from small electrodes inside the heart to later tiers that increasingly use a large electrode surface outside the heart. In the latter tiers, a pre-pulse is added prior to each ATP pulse to reduce the sensation of pain.

DETAILED DESCRIPTION

Overview

Figure 1:
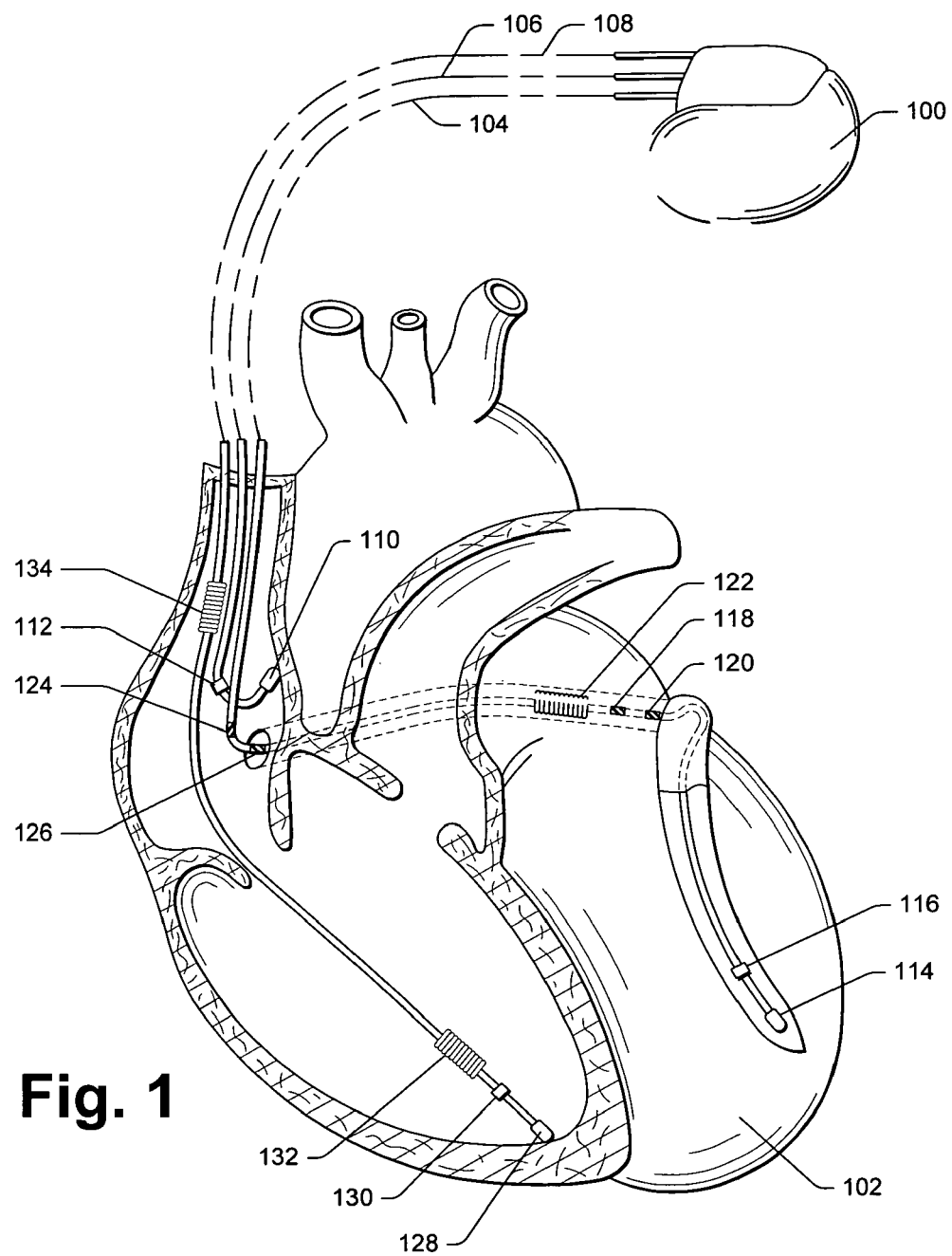
FIG. 1 is a diagram of an exemplary stimulation device in relation to a human heart.

This disclosure describes tiered antitachycardia pacing (ATP), which provides an adaptive and refined therapy for ventricular tachycardia. The tiered ATP divides therapy for ventricular tachycardia into a progression of multiple tiers and may even include a cardioversion tier within the therapy. Some tiers of the tiered ATP may also include pre-pulsing to alleviate pain. The tiered ATP and the pre-pulsing provide an effective and flexible new therapy for ventricular tachycardia.

The tiered ATP therapy includes applying ATP along a progression of different pacing vectors, the progression continuing until the ventricular tachycardia is terminated. If none of the progressive ATP pacing vectors terminate the ventricular tachycardia, then the exemplary tiered ATP therapy culminates in cardioversion.

The exemplary progression of pacing vectors proceeds from a least invasive vector to more invasive vectors, stopping the progression whenever the ventricular tachycardia ceases. In some implementations, the progression of pacing vectors reflects a progression in the size of electrodes used to deliver the ATP, and/or a progression in the area or volume of electrically excitable cardiac tissue to be stimulated. This exemplary technique of tiering the pacing vectors for ATP minimizes pain, especially if the patient is responsive to the least invasive vector. On the other hand, if the patient is relatively non-responsive to the applied ATP, the exemplary tiered ATP technique gradually applies more and more persuasive stimulation before applying cardioversion as a last resort.

To further decrease pain, the exemplary tiered ATP therapy also includes exemplary pre-pulsing, whenever feasible, as an adjunct therapy during use of certain pacing vectors. For example, pre-pulsing can be effective during use of far-field vectors—e.g., unipolar pacing between a ventricular electrode and a far-field electrode outside the heart, such as the relatively distant case of the implanted device, used as an electrode. A pacing "pre-pulse" is a minor pulse preceding a main pacing pulse, applied in order to accomplish "pre-pulse inhibition" (PPI). In one implementation, when pre-pulsing is used, a pre-pulse is applied prior to each antitachycardia pulse in order to decrease the patient's sensation of pain. Pre-pulses are preferably applied over a different vector than the ATP being applied (away from the action) so that the pre-pulsing does not interfere with proper ATP timing. For example, the pre-pulse vector can be anywhere where it will be felt by the patient in order to effect the pre-pulse inhibition of the sensation of pain that would be caused by the applied ATP.

An exemplary system thus applies progressive tiers of ATP, beginning with a mild and least-invasive pacing therapy that may even go unnoticed by the patient. If ventricular tachycardia still persists, the system may apply intermediate pacing therapies of increasing strength and/or more effective but more invasive pacing vectors. If these do not terminate the ventricular tachycardia, then the system progresses to low power or high power cardioversion shocks.

Exemplary Stimulation Device

Before describing the exemplary tiered ATP and exemplary pre-pulsing therapy, an example device by which the tiered ATP and the pre-pulsing can be applied is now described. As shown in FIG. 1, a stimulation device 100 is in electrical communication with a patient's heart 102 by way of three leads, 104, 106 and 108, suitable for delivering multi-chamber stimulation and shock therapy. Not every configuration has all of the illustrated electrodes to be described below, but a particular configuration may include some of these illustrated electrodes. Other configurations of the stimulation device 100 may include even more electrodes than illustrated. For example, the exemplary tiered ATP can be applied by other, additional system electrodes than those illustrated and described below. Additional electrodes for delivering tiered ATP can include combinations or electrodes situated over the epicardium (e.g., multiple pacing and relatively larger surface area defibrillation electrodes that may be used for optimizing cardiac resynchronization therapy (CRT) and providing defibrillation).

Regarding the leads and electrodes that are illustrated in FIG. 1, in order to sense atrial cardiac signals and to provide right atrial chamber stimulation therapy, the stimulation device 100 is coupled to an implantable right atrial lead 106, typically having an atrial tip electrode 110 and an atrial ring electrode 112, which typically is implanted in the patient's right atrial appendage. Stimulation device 100 is also known as and referred to as a pacing device, a pacing apparatus, a cardiac rhythm management device, or an implantable cardiac stimulation device. Stimulation device 100 can be an implantable cardioverter/defibrillator (ICD).

To sense left atrial and ventricular cardiac signals and to provide left chamber pacing therapy, the stimulation device 100 is coupled to a "coronary sinus" lead 104 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 104 is designed to receive atrial and ventricular cardiac signals and to deliver left ventricular pacing therapy using a left ventricular (LV) tip electrode 114 and a LV ring electrode 116. Left atrial pacing therapy uses, for example, first and second left atrial (LA) ring electrodes 118 and 120. Shocking therapy can be performed using at least a left atrial (LA) coil electrode 122. For a description of an exemplary coronary sinus lead, see U.S. Pre-Grant Publication No. 2003/0050681, "A Self-Anchoring Coronary Sinus Lead" (Pianca et al.), and U.S. Pat. No. 5,466,254 to Helland, entitled, "Coronary Sinus Lead with Atrial Sensing Capability," which patent documents are incorporated herein by reference. Coronary sinus lead 104 may also include a pair of right atrial (RA) ring electrodes 124 and 126, which may be used to provide right atrial chamber pacing therapy.

The stimulation device 100 is also shown in electrical communication with the patient's heart 102 by way of an implantable right ventricular lead 108, typically having an right ventricular (RV) tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
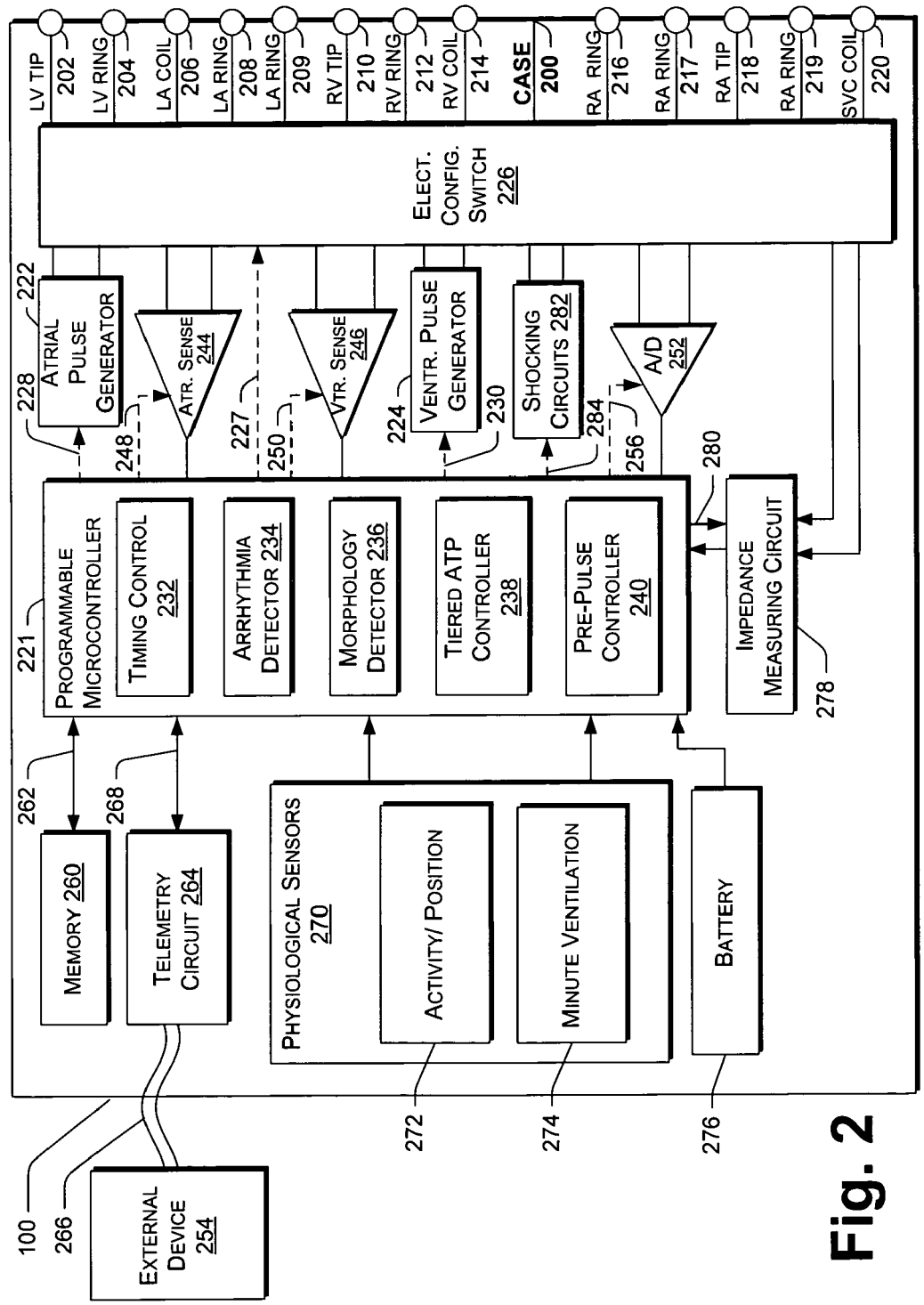
FIG. 2 is a block diagram of components of the exemplary stimulation device of FIG. 1.

FIG. 2 shows an exemplary block diagram depicting various components of the exemplary stimulation device 100.

The components are typically contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 122, 132, 134 for stimulating purposes. The case 200 further includes a connector (not shown) having a plurality of terminals (202, 204, 206, 208, 209, 210, 212, 214, 216, 217, 218, 219, and 220—shown schematically with the names of the electrodes to which they are connected shown next to the terminals), including:

a left ventricular tip terminal (LV TIP) 202 for left ventricular tip electrode 114;

a left ventricular ring terminal (LV RING) 204 for left ventricular ring electrode 116;

a left atrial shocking terminal (LA COIL) 206 for left atrial coil electrode 122;

a left atrial ring terminal (LA RING) 208 for left atrial ring electrode 118;

a left atrial ring terminal (LA RING) 209 for left atrial ring electrode 120;

a right ventricular tip terminal (RV TIP) 210 for right ventricular tip electrode 128;

a right ventricular ring terminal (RV RING) 212 for right ventricular ring electrode 130;

a right ventricular shocking terminal (RV COIL) 214 for RV coil electrode 132;

a right atrial ring terminal (RA RING) 216 for atrial ring electrode 124;

a right atrial ring terminal (RA RING) 217 for right atrial ring electrode 126;

a right atrial tip terminal (RA TIP) 218 for atrial tip electrode 110;

a right atrial ring terminal (RA RING) 219 for atrial ring electrode 112;

a SVC shocking terminal (SVC COIL) 220 for right atrial SVC coil electrode 134.

An exemplary stimulation device 100 may include a programmable microcontroller 221 that controls various operations of the stimulation device 100, including cardiovascular monitoring, hemodynamic monitoring, and cardiovascular stimulation therapy. Microcontroller 221 includes a microprocessor (or equivalent control circuitry), RAM and/or ROM memory, logic and timing circuitry, state machine circuitry, and I/O circuitry.

The exemplary stimulation device 100 may further include an atrial pulse generator 222 and a ventricular pulse generator 224 that generate pacing stimulation pulses for delivery by the right atrial lead 106, the coronary sinus lead 104, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 221, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 221 via appropriate control signals 228 and 230, respectively, to trigger or inhibit the stimulation pulses.

Microcontroller 221 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 221 may also implement an arrhythmia detector 234, a morphology detector 236, a tiered ATP controller 238 for applying tiered antitachycardia pacing in response to ventricular tachycardia, and a pre-pulse controller 240 for applying pre-pulses to the antitachycardia pacing to relieve pain associated with the antitachycardia pacing that is applied during at least one of the tiers of the tiered antitachycardia pacing. The microcontroller 221 may process input from physiological sensors 270, such as accelerometers of an activity/position module 272, and a minute ventilation module 274, etc., The components 234, 236, 238, and 240 may be implemented in hardware as part of the microcontroller 221, or as software/firmware instructions programmed into an implementation of the stimulation device 100 and executed on the microcontroller 221 during certain modes of operation. Although not shown, the microcontroller 221 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 106, coronary sinus lead 104, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary stimulation device 100 to sense low amplitude signal characteristics of atrial or ventricular fibrillation.

The outputs of the atrial and ventricular sensing circuits 244 and 246 are connected to the microcontroller 221 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 221 over signal lines 248 and 250 to control, for example, the gain and/or threshold of polarization charge removal circuitry (not shown) and the timing of blocking circuitry (not shown) optionally coupled to the inputs of the sensing circuits 244, 246.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 106, the coronary sinus lead 104, and the right ventricular lead 108 through the switch 226 to sample cardiac signals across any pair of desired electrodes.

The data acquisition system 252 is coupled to the microcontroller 221, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 221 detects a depolarization signal during a window following a stimulation pulse, the presence of which indicates that capture has occurred. The microcontroller 221 enables capture detection by triggering the ventricular pulse generator 224 to generate a stimulation pulse, starting a capture detection window using the timing control circuitry 232 within the microcontroller 221, and enabling the data acquisition system 252 via control signal 256 to sample the cardiac signal that falls in the capture detection window and, based on the amplitude, determines if capture has occurred.

The microcontroller 221 is further coupled to a memory 260 by a suitable data/address bus 262. The programmable operating parameters used by the microcontroller 221 are stored in memory 260 and used to customize the operation of the exemplary stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the exemplary stimulation device 100 may be non-invasively programmed into the memory 260 through a telemetry circuit 264 in telemetric communication via communication link 266 with the external device 254, such as a programmer, local transceiver, or a diagnostic system analyzer. The microcontroller 221 can activate the telemetry circuit 264 with a control signal 268. The telemetry circuit 264 allows intracardiac electrograms and status information relating to the operation of the exemplary stimulation device 100 (as contained in the microcontroller 221 or memory 260) to be sent to the external device 254 through an established communication link 266.

The physiological sensors 270 referred to above can further include, for example, "rate-responsive" sensors that adjust pacing stimulation rates according to the exercise state of the patient. Accordingly, the microcontroller 221 responds by adjusting the various pacing parameters (such as rate, AV Delay, V-V Delay, etc.) at which the atrial and ventricular pulse generators 222 and 224 generate stimulation pulses.

The physiological sensors 270 may include mechanisms and sensors to detect bodily movement (272), minute ventilation 274, changes in blood pressure, changes in cardiac output, changes in the physiological condition of the heart, diurnal changes in activity (e.g., detecting sleep and wake states), G-force acceleration of the ICD case 200, length of the cardiac QT interval, blood oxygen saturation, blood pH, changes in temperature, respiration rate, and QRS wave duration. While shown as being included within the exemplary stimulation device 100, the physiological sensor(s) 270 may also be external to the exemplary stimulation device 100, yet still be implanted within or carried by the patient, e.g., a blood pressure probe. Examples of physiological sensors external to the case 200 that may be deployed by stimulation device 100 include sensors that, for example, sense respiration activities, $O_2$ saturation, evoked response, pH of blood, and so forth.

The illustrated physiological sensors 270 include one or more activity/position sensors 272 (e.g., 1D or 3D accelerometers, movement sensors, etc.) to detect changes in the patient's position. The activity/position sensors 272 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 274 may also be included in the physiological sensors 270 in order to sense rate and depth of breathing. Minute ventilation can be measured as the total volume of air that moves in and out of a patient's lungs in a minute. The MV sensor 274 may use an impedance measuring circuit 278 to sense air movement by measuring impedance across the chest cavity.

The impedance measuring circuit 278 is enabled by the microcontroller 221 via a control signal 280 and can be used for many things besides the abovementioned detection of air movement in and out of the lungs, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used.

The exemplary stimulation device 100 additionally includes a battery 276 that provides operating power to all of the components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has predictable discharge characteristics so that elective replacement time can be detected. As one example, the exemplary stimulation device 100 employs lithium/silver vanadium oxide batteries.

The exemplary stimulation device 100 can further include magnet detection circuitry (not shown), coupled to the microcontroller 221, to detect when a magnet is placed over the exemplary stimulation device 100. A magnet may be used by a clinician to perform various test functions of the exemplary stimulation device 100 and/or to signal the microcontroller 221 that an external programmer (e.g., 254) is in place to receive or transmit data to the microcontroller 221 through the telemetry circuits 264.

The microcontroller 221 further controls a shocking circuit 282 via a control signal 284. The shocking circuit 282 generates shocking pulses of low (e.g., up to 0.5 joules), moderate (e.g., 0.5-10 joules), or high energy (e.g., 11-40 joules), as selected by the microcontroller 221. Such shocking pulses are applied to the patient's heart 102 through at least two shocking electrodes selected, for example, from the left atrial coil electrode 122, the RV coil electrode 132, and/or the SVC coil electrode 134. As noted above, the case 200 may act as an active electrode in combination with the RV coil electrode 132, or as part of a split electrical vector using the SVC coil electrode 134 or the left atrial coil electrode 122 (i.e., using the RV coil electrode 132 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 221 is capable of controlling the synchronous or asynchronous delivery of the shocking pulses.

More generally, the exemplary stimulation device 100 can be programmed to stimulate different sets of vascular and cardiac muscles through the same lead/electrode system. The exemplary stimulation device 100 can be programmed to vary the output voltage of various pulses to effectively stimulate different muscles of the heart and blood vessels, even though the physical placement of leads and electrodes does not change.

Exemplary Tiered ATP

Before starting any antitachycardia therapy, a stimulation device 100 capable of applying the exemplary tiered ATP first determines that ventricular tachycardia is occurring. Then the stimulation device 100 begins the exemplary tiered progression of pacing vectors introduced above. The exemplary sequence of tiered ATP that will now be described with respect to FIGS. 3-9 (and FIG. 10) is provided as one example sequence of the tiered ATP approach. More particularly, the specific electrodes selected in each of the following figures to create a progression of one or more electrical vectors do not constitute the essence of the exemplary tiered ATP technique, but only provide one example of various electrode combinations that can be used to implement an instance of tiered ATP. Other electrodes can, and likely would, be used in actual implementations. For example, one or more tiers of the exemplary tiered ATP can use other, additional, system electrodes, e.g., that may be situated over the epicardium. These may include relatively large surface area defibrillation electrodes that may be in place for optimizing CRT and/or providing defibrillation; subcutaneous electrode patches or coil arrays, etc. Moreover, alternative implementations may utilize one or more coronary sinus coil electrodes to deliver ATP in one or more of the exemplary tiers, or may use various combinations of pacing electrodes.

Figure 3:
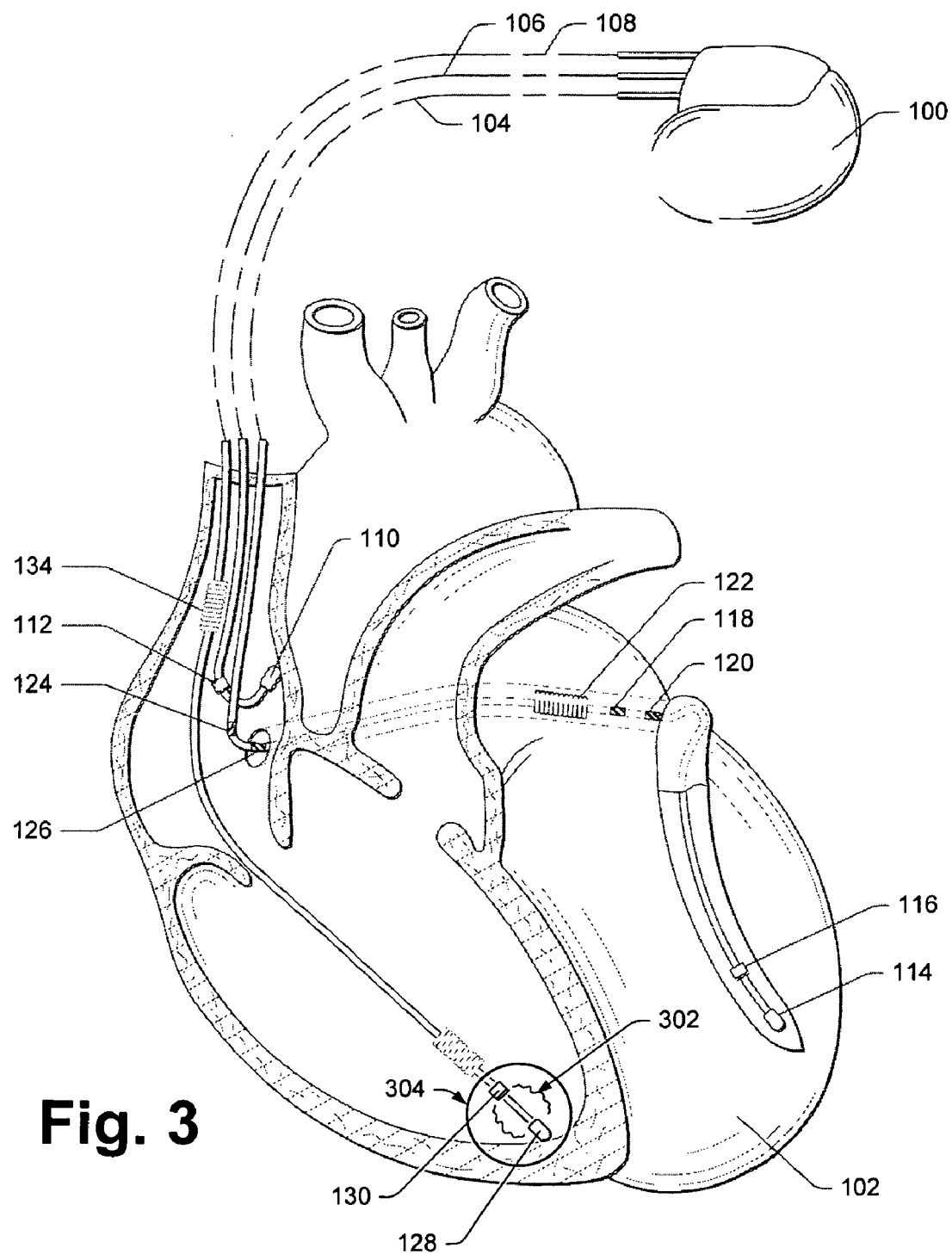
FIG. 3 is a diagram of an exemplary first tier of exemplary tiered antitachycardia pacing (ATP).

FIG. 3 shows a first tier of exemplary tiered ATP. The exemplary tiered ATP controller 238 establishes a first-tier pacing vector 302 between typical electrodes used for pacing in either the left ventricle, the right ventricle, or both ventricles. For example, the first tier pacing vector may be established between the RV tip electrode 128 and the RV coil electrode 132. The tiered ATP controller 238 may select electrodes via the electrode configuration switch 226 of the exemplary stimulation device 100. The exemplary stimulation device 100 then delivers ATP through these pacing electrodes. U.S. Pat. No. 6,731,982 to Kroll and Fain, entitled, "Antitachycardia pacing methods and devices," which is incorporated herein by reference, describes various implementations for applying pacing that can be used herein as the first tier of the exemplary tiered ATP. The volume of electrically excitable cardiac tissue 304 directly affected by the first-tier pacing vector 302 is relatively small in comparison to the heart 102 itself.

For some of the tiers of the exemplary tiered ATP, the exemplary tiered ATP controller 238 may implement the most common form of ATP, "burst pacing." Burst pacing delivers multiple pacing pulses (i.e., a burst of pulses) at a cycle length between approximately 50-100% of the tachycardia cycle length (and even more typically between approximately 70-90% of the tachycardia cycle length). Cycle length is also sometimes called the "coupling interval." For example, delivering pulses having an 80% cycle length is also known as delivering pulses having an 80% coupling interval.

Each burst of pacing pulses typically includes 2-20 pulses. The number of bursts used is typically 1-15. The rate of each burst can either be a fixed predetermined rate (i.e., fixed burst) or a rate that is calculated based on the rate of the ventricular tachycardia being treated (adaptive burst). The risk of accelerating the tachycardia is minimized by keeping the number of pulses in a burst to a minimum (i.e., the minimum number postulated to terminate the ventricular tachycardia) and also by minimizing the rate of the burst and the anticipated total number of bursts needed to terminate the ventricular tachycardia.

Many ATP regimens employ variations on the basic theme of burst pacing. Thus, in one variation, the exemplary tiered ATP controller 238 may deliver the first tier ATP by simultaneously pacing the right ventricle and the left ventricle, but independently of each other. This can be accomplished, for example, by triggering the LV pace/sense electrode pair (e.g., LV ring 116 and LV tip 114) based on a sensed signal produced by the LV pace/sense pair, and triggering the RV pace/sense electrode pair (e.g., RV ring 130 and RV tip 128) based on a separate sensed signal produced by the RV pace/sense pair. This means that the timing of at least a first pacing pulse (e.g., in a burst of antitachycardia pacing pulses) is based on the corresponding sensed signal. Timing of additional pulses (e.g., in the burst) can also be based on the sensed signal. Alternatively, timing of additional pulses can be based on a predetermined or calculated coupling interval.

So, at the first tier of the exemplary tiered ATP, the tiered ATP controller 238 determines a train of pulses, including the number of bursts to apply through the typical pacing electrodes (e.g., 128, 130), the number of pulses per burst, and the cycle length of the pulses. After applying the train of pulses, the exemplary stimulation device 100 checks for the persistence of the ventricular tachycardia. If the tachycardia has not been terminated, then the tiered ATP controller 238 proceeds to a second tier of the exemplary tiered ATP.

Figure 4:
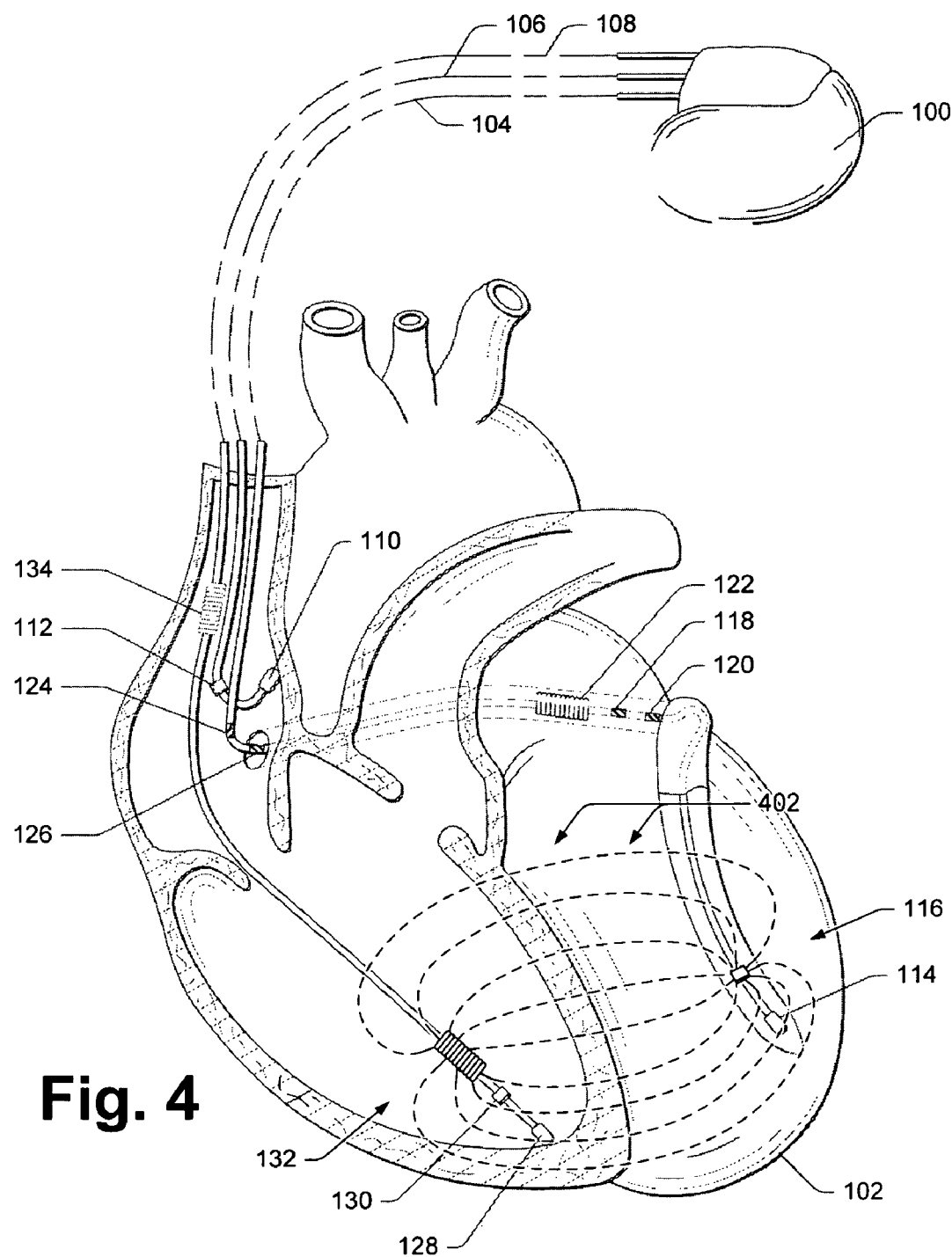
FIG. 4 is a diagram of an exemplary second tier of the tiered ATP.

FIG. 4 shows the second tier of the exemplary tiered ATP. If ventricular tachycardia persists, in one implementation, the tiered ATP controller 238 escalates to delivering the ATP between the LV ring electrode 116 and the RV coil electrode 132 to form a second-tier pacing vector 402. The second-tier pacing vector 402 provides greatly improved electrical fields and increases the opportunities for the paced wavefront to couple across even more of the excitable cardiac tissue than in the first tier. With the better field from the larger scale electrodes, a higher percentage of the tissue is captured electronically (or instantly), thus increasing the chances of converting the ventricular tachycardia to a normal sinus rhythm.

Delivering the pulses between the LV ring electrode 116 and the RV coil electrode 132 keeps most of the applied electrical current within the heart, thus keeping pain and discomfort to a minimum. For the same reason, this is also one of several possible vectors that provides efficient use of the implanted device's energy resources in view of the amount of tissue that it can potentially capture per energy expended. Rarely, some patients may experience phrenic nerve capture from this vector because of the nerve's proximity. It should be noted that alternate electrodes can be substituted for either the RV coil electrode 132 or the LV ring electrode 116. For example, in an advanced ICD system that offers a small LV coil electrode, the ATP of this tier could be delivered between the LV coil electrode and the RV coil electrode 132.

After applying the second-tier pacing, the stimulation device 100 again checks for the persistence of ventricular tachycardia. If the tachycardia has not been terminated, the tiered ATP controller 238 proceeds to a third tier of the exemplary tiered ATP.

Figure 5:
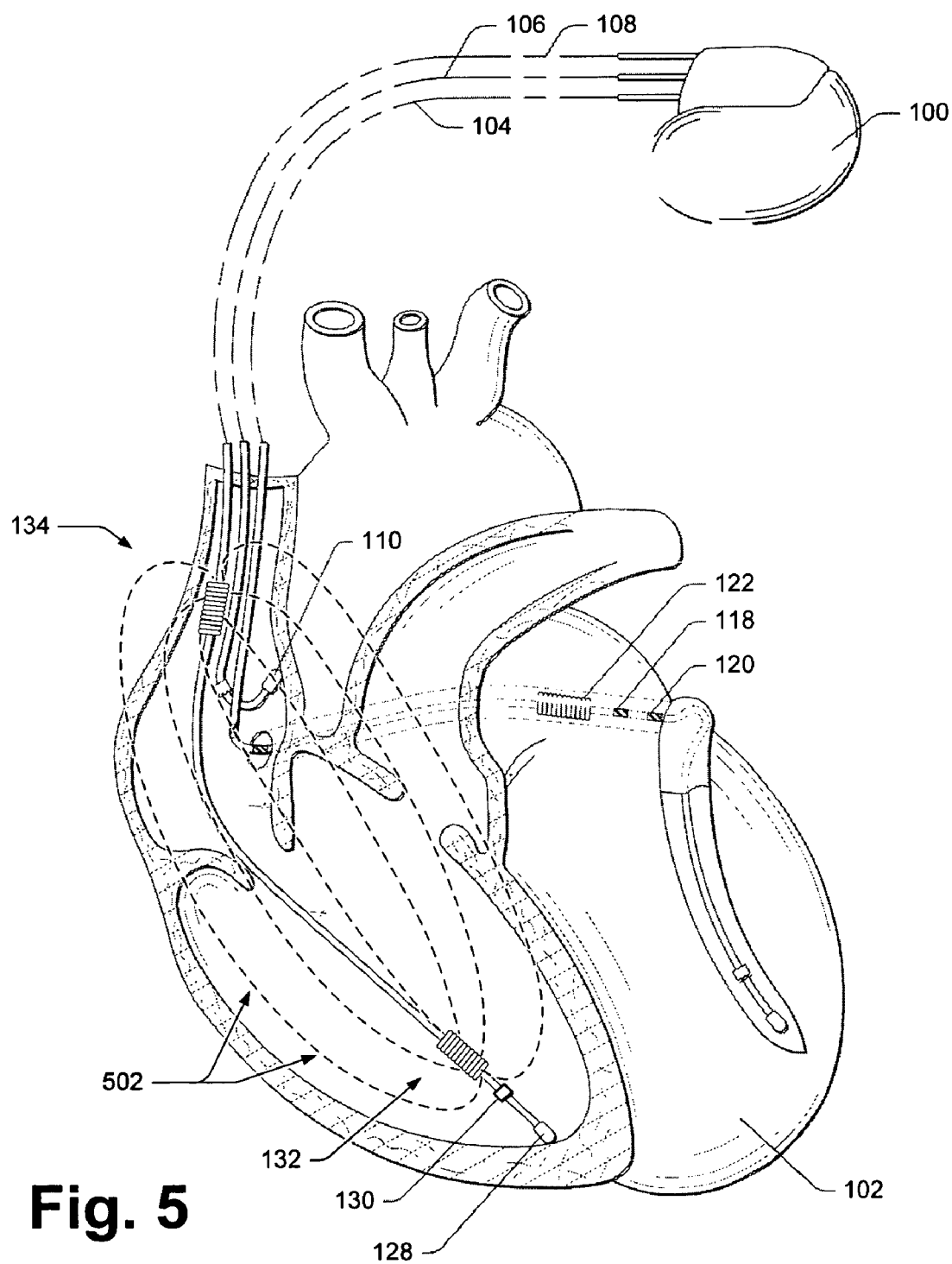
FIG. 5 is a diagram of an exemplary third tier of the tiered ATP.

FIG. 5 shows the third tier of the exemplary tiered ATP. If ventricular tachycardia still persists even after the first and second tiers, the tiered ATP controller 238 now proceeds to delivering the ATP between the RV coil electrode 132 and the SVC coil electrode 134 to form a third-tier pacing vector 502. The third-tier pacing vector 502 provides different vectors from the second tier pacing and different areas of capture in the left ventricle and especially in the right ventricle. The pain and discomfort to patients should still be relatively minimal, although the SVC coil electrode 134 does sometimes protrude outside of the heart—i.e., in the superior vena cava.

Figure 6:
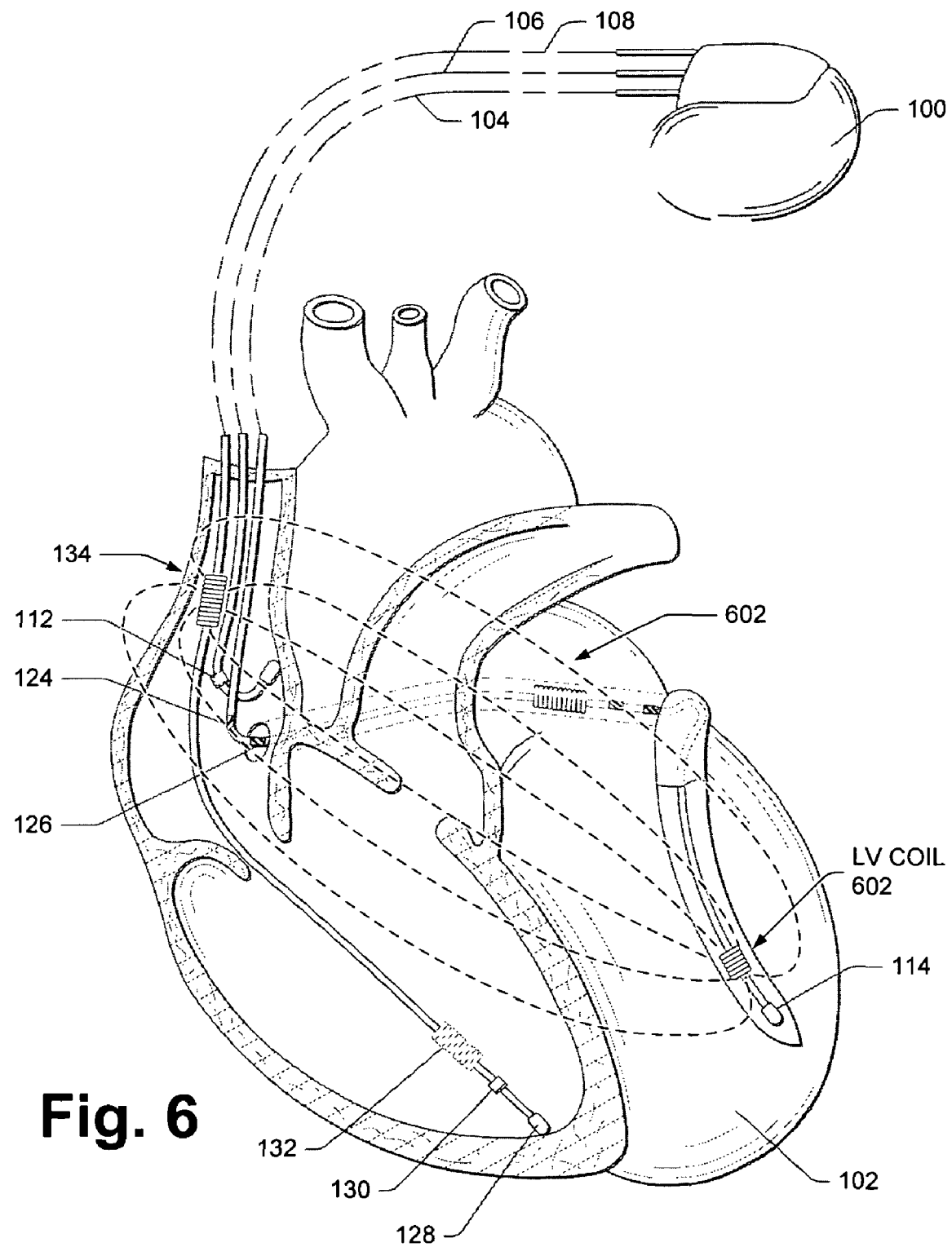
FIG. 6 is a diagram of an exemplary alternative third tier of the tiered ATP.
Figure 7:
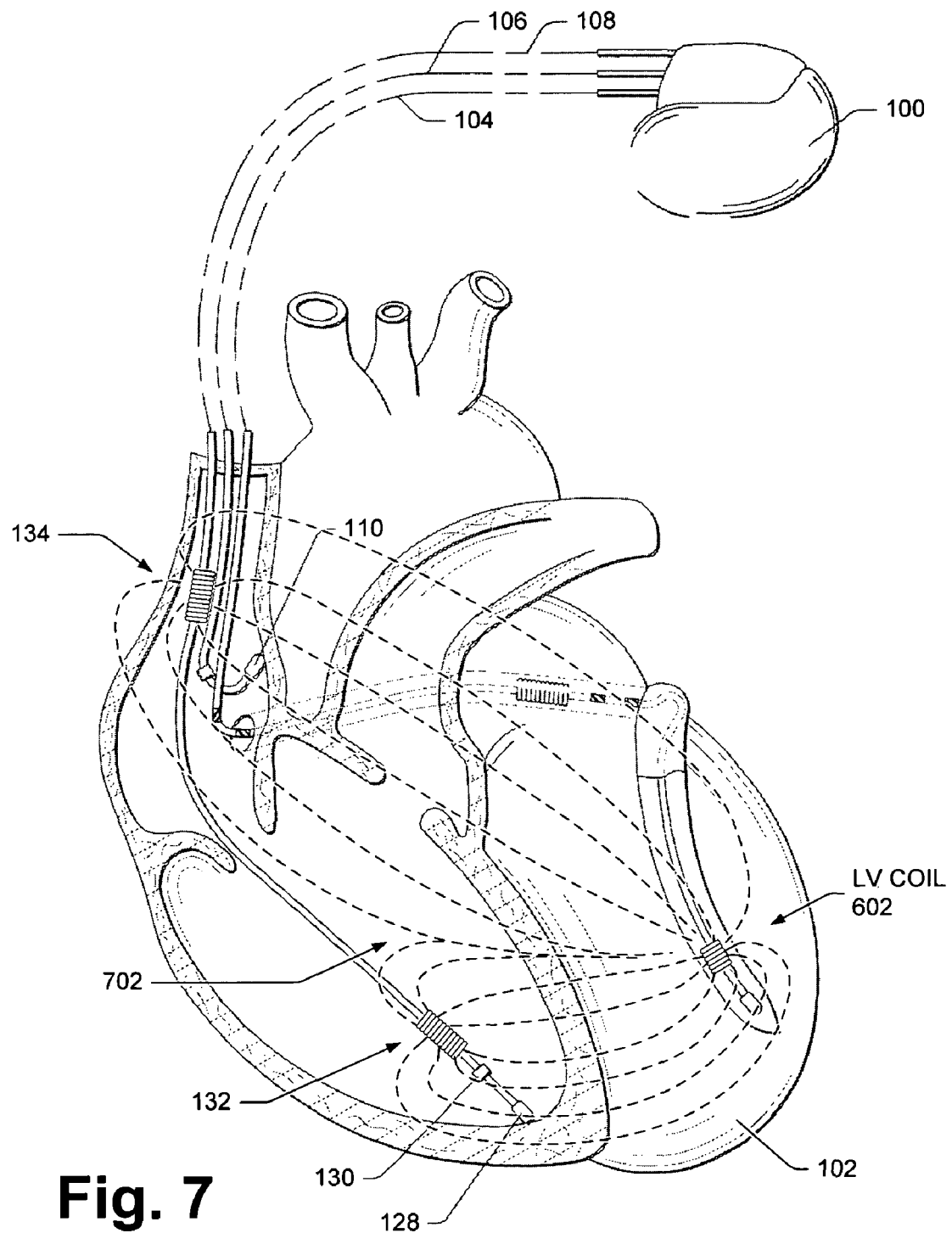
FIG. 7 is a diagram of another exemplary alternative third tier of the tiered ATP.

Alternatively, as shown in FIG. 6, the third-tier ATP can be delivered between an LV coil electrode 602 and the SVC coil electrode 134 to form an alternative third-tier pacing vector 602. Or, in another variation, as shown in FIG. 7, the third-tier ATP can be delivered along another alternative third-tier pacing vector 702, between an LV coil electrode 602 and a parallel combination of the RV coil electrode and SVC coil. This provides a useful split electrical vector 702. Such a pacing vector 702 is especially attractive for a ventricular tachycardia that has a focus located superiorly in the basal left ventricle.

After applying the third-tier pacing, the stimulation device 100 again checks for the enduring presence of ventricular tachycardia. If the tachycardia has not been terminated, then the tiered ATP controller 238 proceeds to a fourth tier of the exemplary tiered ATP.

Figure 8:
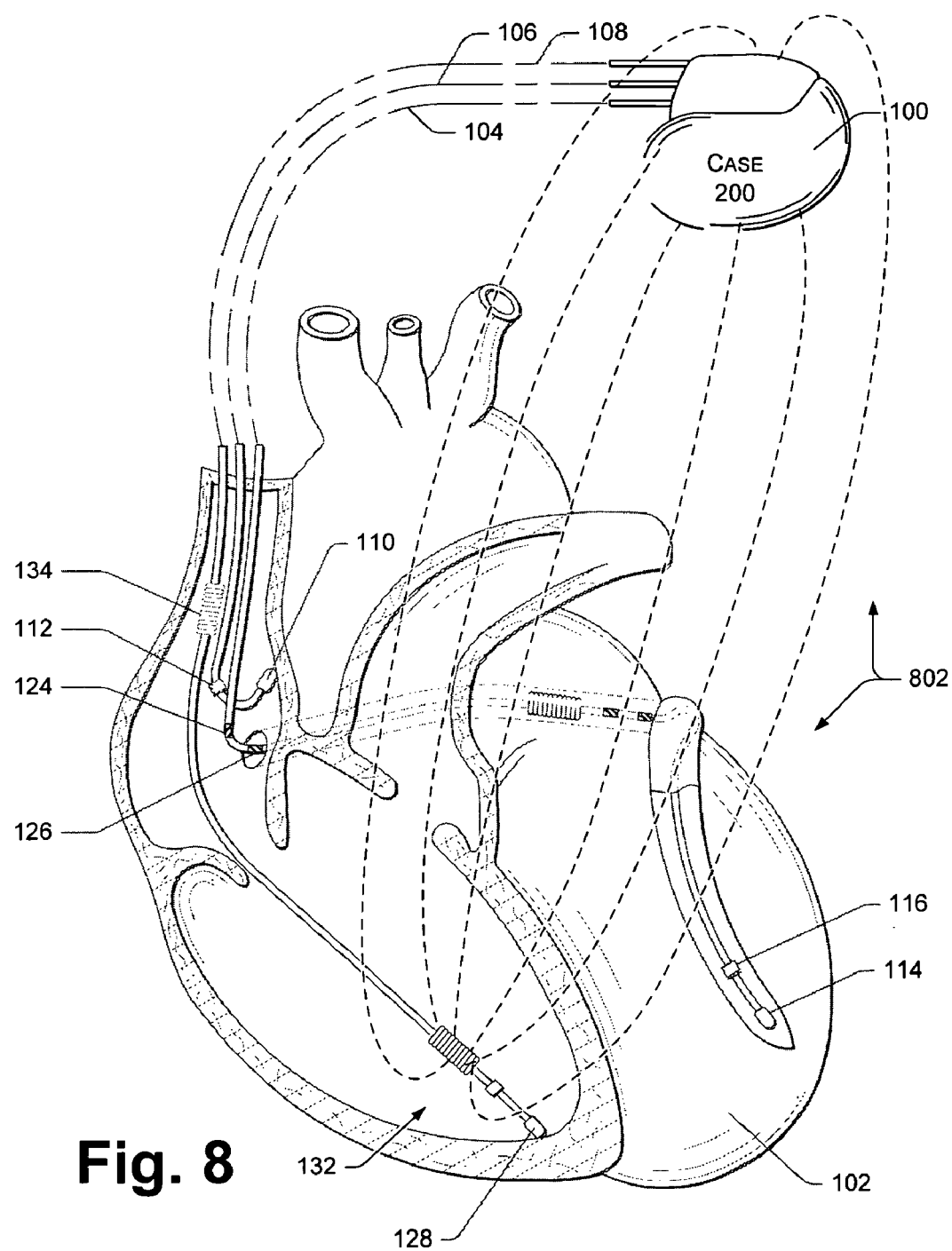
FIG. 8 is a diagram of an exemplary fourth tier of the tiered ATP.

FIG. 8 shows the fourth tier of the exemplary tiered ATP. If ventricular tachycardia is still present despite application of ATP along the first, second, and third tier pacing vectors, the tiered ATP controller 238 again steps up the therapy by delivering the ATP between the case 200 and the RV coil electrode 132 to form a fourth-tier pacing vector 802. This gives a broad "far-field" electrical stimulation. In some implementations, far-field ATP can be applied as described in U.S. Pat. No. 5,243,978 to Duffin or U.S. Pat. No. 5,330,509 to Kroll. To decrease pain, however, as the case 200 is an electrode outside the heart, exemplary pre-pulsing therapy can also be applied, as will be described further below.

Figure 9:
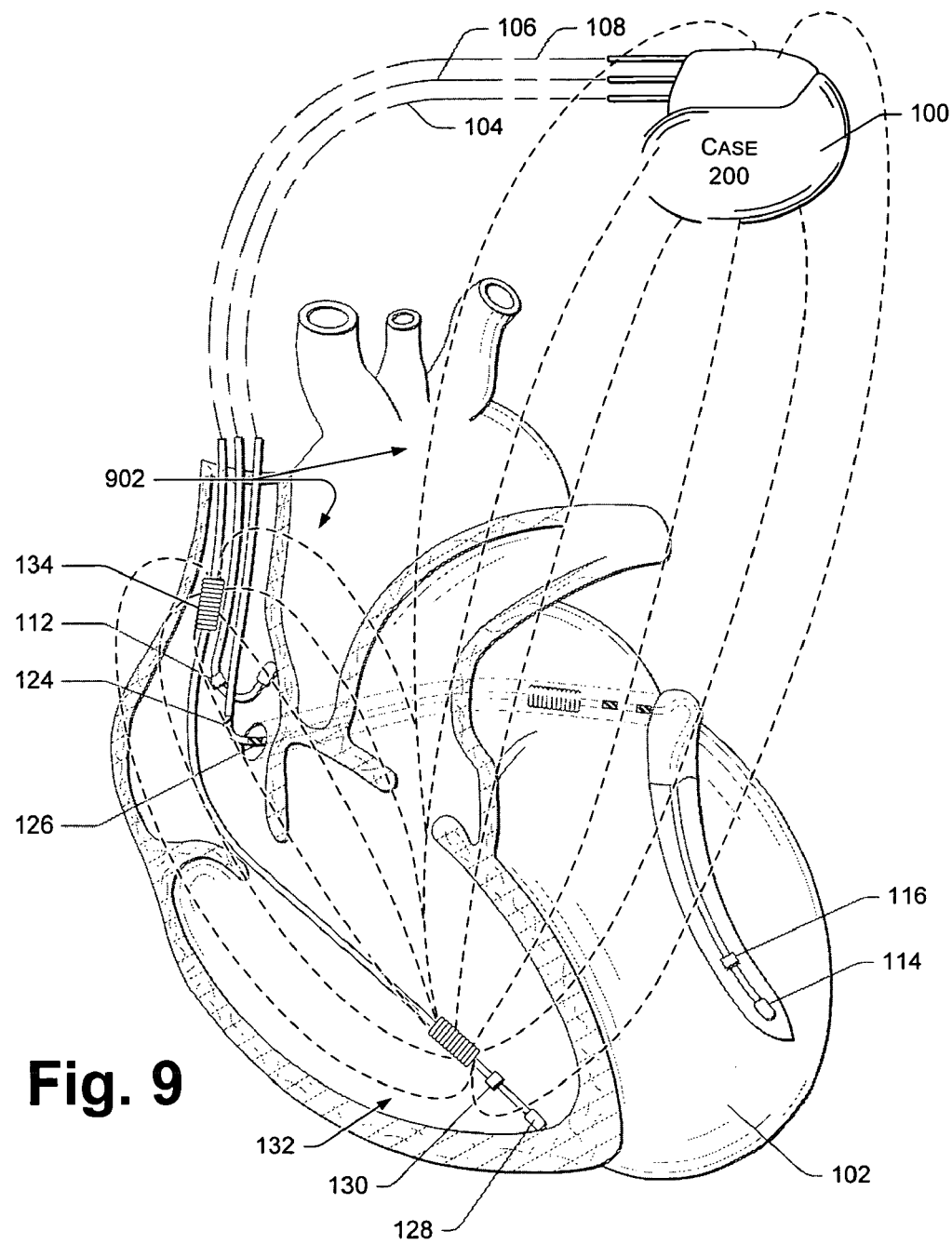
FIG. 9 is a diagram of an exemplary alternative fourth tier of the tiered ATP.

Alternatively, as shown in FIG. 9, the fourth-tier ATP can be delivered between a parallel combination of the SVC coil electrode 134 and the case 200, down to the RV coil electrode 132 as the common electrode. Resulting fourth-tier pacing vectors 902 provide an elegant, fairly homogeneous field coverage of the entire left ventricle and should be very successful at converting difficult ventricular tachycardias. However, involvement of the case 200 almost guarantees patient perception of the applied ATP and many patients would likely find this sensation very uncomfortable. This is due to extra nerves that respond to stimulation when the case 200 is an electrode. However, these fourth-tier pacing vectors 902 should still be significantly more preferable to patients than a high-energy shock, and as mentioned above, this far-field fourth-tier ATP can be accompanied by pre-pulsing therapy, to be described in greater detail further below.

Figure 10:
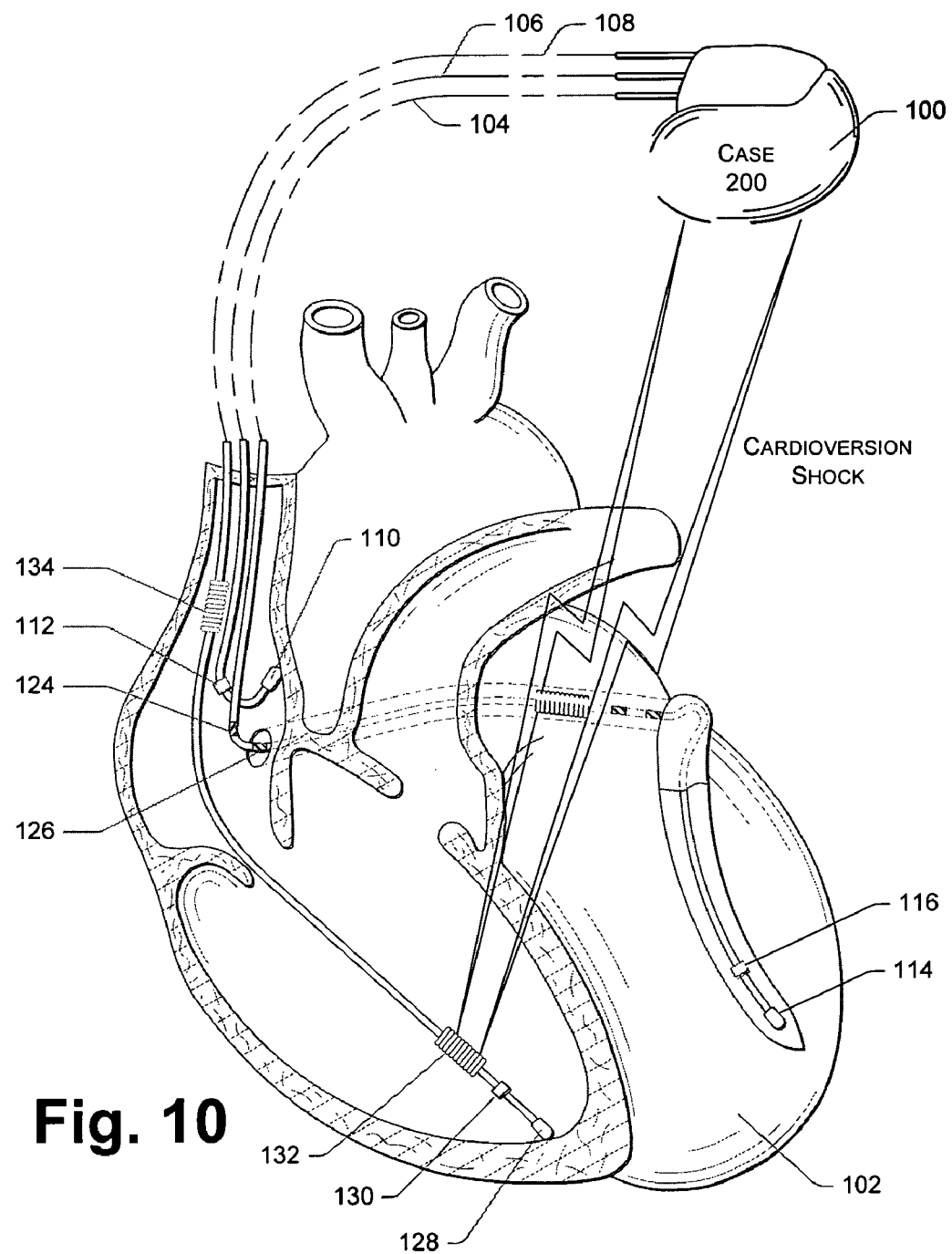
FIG. 10 is a diagram of an exemplary fifth tier of the tiered ATP.

After applying the fourth-tier pacing, the stimulation device 100 again checks for the persistence of ventricular tachycardia. As shown in FIG. 10, if the ventricular tachycardia has still not been terminated, then the tiered ATP controller 238 proceeds to a fifth-tier of the therapy that consists of delivering one or more cardioversion shocks.

Exemplary Pre-Pulsing Therapy

In the higher tiers of the tiered ATP, delivering ATP with high currents across large electrodes is an effective way to treat high rate ventricular tachycardias that are difficult to terminate. However, the use of such electrodes—especially the case 200 of the stimulation device 100—can cause significant pain and discomfort for the patient, especially when the pulse voltages are in the range of approximately 10-20 volts. This pain and discomfort is an even greater problem for a cardioverter defibrillator that uses subcutaneous electrode action.

For certain of the pacing vectors corresponding to the higher tiers of the exemplary tiered ATP, the pre-pulse controller 240 of the exemplary stimulation device 100 may add a pre-pulse before each antitachycardia pacing pulse in order to decrease pain. For example, when the case 200 of the stimulation device 100 is used for far-field ATP, the added pre-pulsing therapy may greatly decrease the perception of pain that can usually accompany far-field pacing. From another perspective, the exemplary pre-pulsing therapy allows the use of high current ATP, which is effective for terminating difficult ventricular tachycardias, by decreasing pain and discomfort so that the patient can better tolerate the high current pulses.

The perceived intensity of abrupt and startling high current pacing pulses from far-field pacing outside the heart can be diminished by delivering a weaker pre-pulse approximately 30-500 milliseconds (ms) prior to each of the main, high current pulses, as described in U.S. Pat. No. 6,711,442 to Swerdlow et al, "Method and Apparatus for Reduction of Pain from Electric Stimulation Therapies," which is incorporated herein by reference. Physiologic suppression of the perception of pain in this manner is called "pre-pulse inhibition" (PPI). Thus, pre-pulsing therapy decreases both the motor response and the patient's higher perception of the intensity of the startling and painful pacing pulses. With respect to the neural circuits, PPI reflects the activation of "hard-wired" behavioral gating processes that reduce the sensation of pain and are regulated by forebrain neural circuitry. Pre-pulses are preferably applied over a different vector than the ATP being applied (away from the action) so that the pre-pulsing does not interfere with proper ATP timing. For example, the pre-pulse vector can be anywhere where it will be felt by the patient in order to effect the inhibition of pain that would be caused by the applied ATP.

Figure 11:
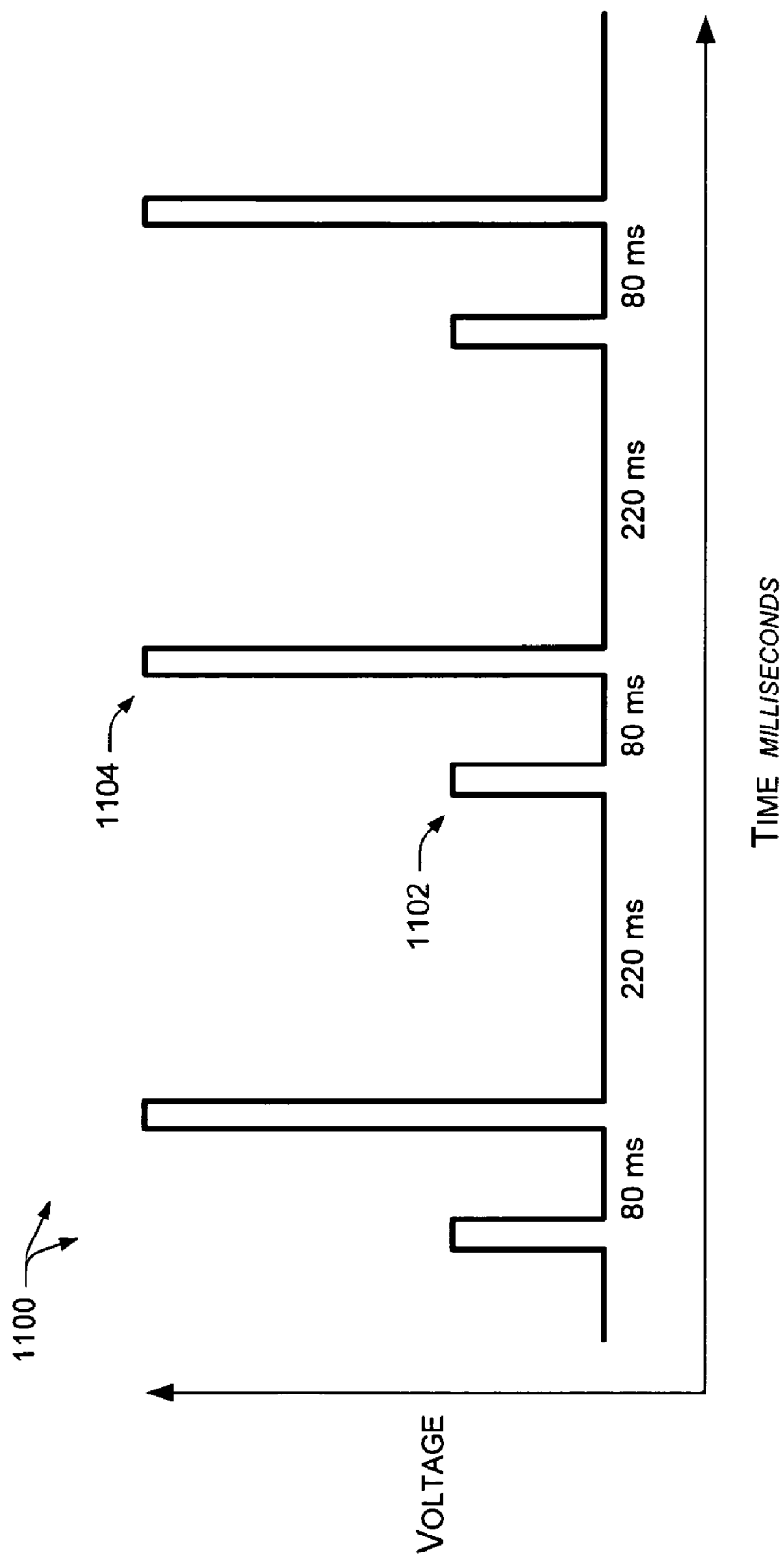
FIG. 11 is a diagram of an exemplary pre-pulsing waveform.

FIG. 11 shows an exemplary waveform 1100 for the pre-pulsing therapy. The smaller pulse preceding each larger pulse is the pre-pulse 1102. In one implementation, each pre-pulse 1102 is on the order of approximately 12 volts between the case 200 of the exemplary stimulation device 100 and the RV coil electrode 132. Approximately 80 milliseconds later, the main pulse 1104 is delivered. For example, each main pulse 1104 can be approximately 30 volts between the case 200 and the RV coil electrode 132. Then, there is a gap or interval before this pulsing cycle starts over again, for example, approximately 220 milliseconds. This example waveform 1100 provides an ATP pacing rate of approximately 200 pulses per minute, which is a typical rate chosen to outrun many ventricular tachycardias.

Exemplary Methods

Figure 12:
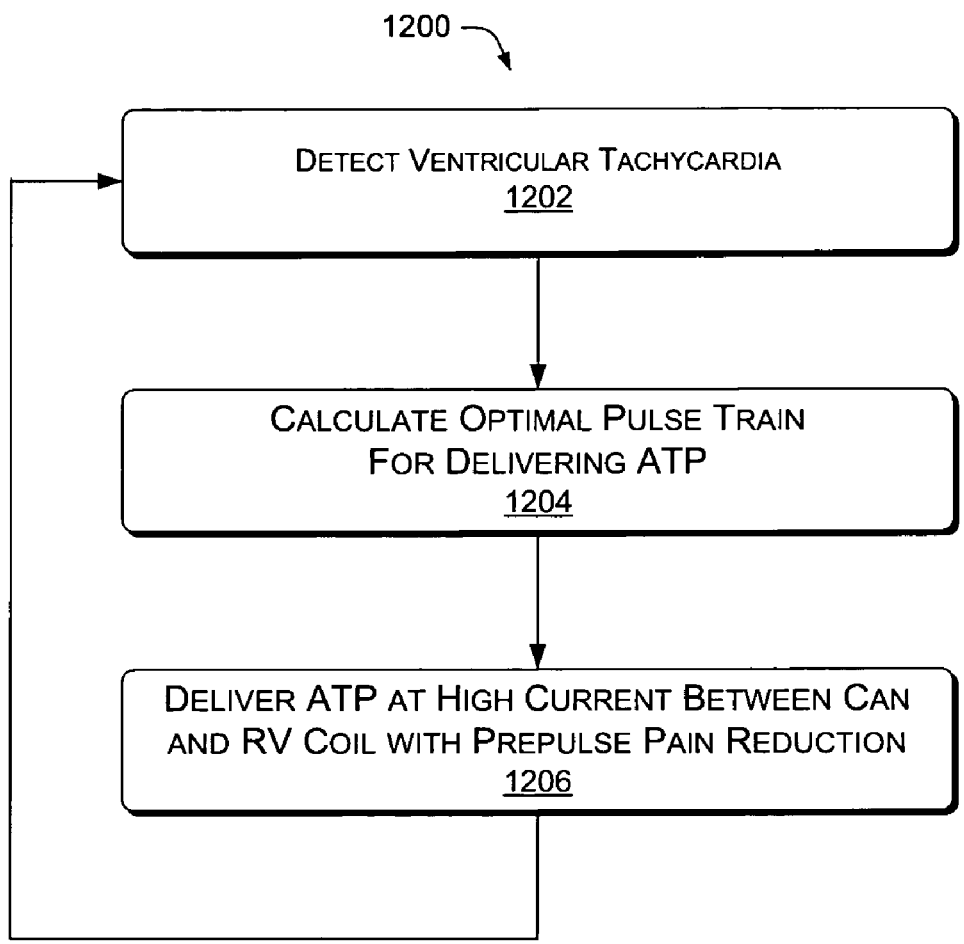
FIG. 12 is a flow diagram of an exemplary method of providing pre-pulsing therapy.

FIG. 12 shows an exemplary method 1200 of providing pre-pulsing therapy, e.g., during ATP, using a far-field electrode. The exemplary method 1200 may be implemented in connection with many suitably configured stimulation devices, although it will be described as being executed by the exemplary pre-pulse controller 240 of the exemplary stimulation device 100. In the flow diagram of FIG. 12, the operations are summarized in individual blocks. Some operations may be performed in hardware and/or as machine-readable instructions (software or firmware) that can be executed by a processor, such as microcontroller 221.

At block 1202, the method 1200 begins by detecting a ventricular tachycardia. For example, the ventricular sensing circuit 246 and arrhythmia detector 234 components of the exemplary stimulation device 100 may detect the ventricular tachycardia. The detection may be the initial detection of the ventricular tachycardia, or one of many detections during tiered ATP that try to decide whether ventricular tachycardia still persists or instead has been terminated by a tier of the applied therapy.

At block 1204, an optimal pulse train for delivering the ATP is calculated. In one implementation, the number of bursts, the number of pulses per burst, the voltage and current of each pulse, and the timing between pulses are calculated. This may be performed by a tiered ATP controller 238 or other components of the exemplary stimulation device 100. In this method 1200, calculating an optimal pulse train also includes adding a pre-pulse for each pacing pulse, to reduce pain and discomfort. This may be performed by the pre-pulse controller 240. When pre-pulsing therapy is added to the calculation, then the voltage and current of the pre-pulses are also calculated as are the time intervals between pre-pulses and main pulses.

At block 1206, the method 1200 delivers the calculated pulse train (ATP and pre-pulses) to the patient. For example, because the pre-pulses reduce pain, the pulse train may be applied at high current between the case 200 of the exemplary stimulation device 100 and the RV coil electrode 132 to provide a very effective ATP while also performing pre-pulse pain reduction.

Figure 13:
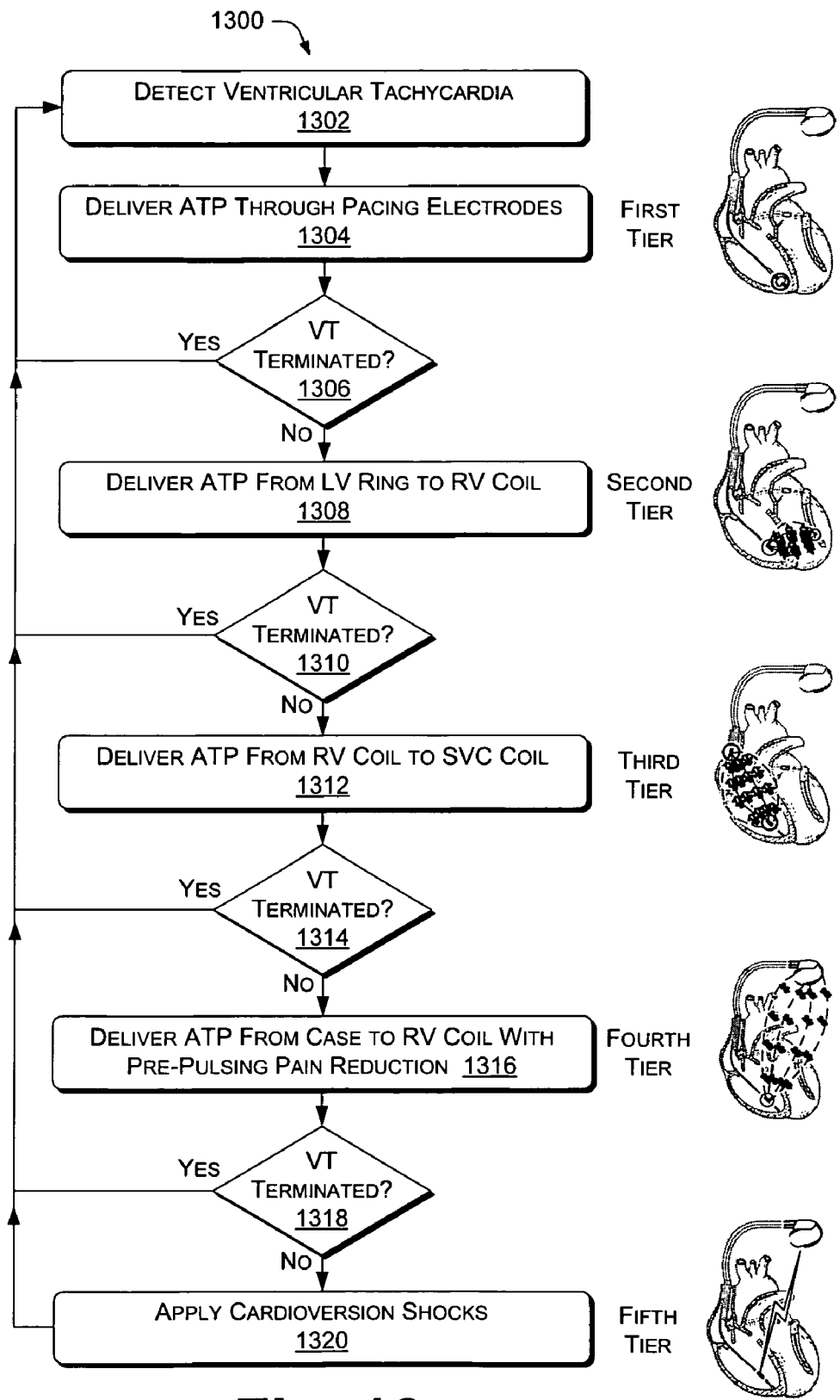
FIG. 13 is a flow diagram of an exemplary method of providing tiered ATP.

FIG. 13 shows an exemplary method 1300 of providing tiered ATP. The exemplary method 1300 may be implemented in connection with many suitably configured stimulation devices, although it will be described as being executed by the exemplary tiered ATP controller 238 of the exemplary stimulation device 100. The particular electrode combinations selected to describe the exemplary method 1300 merely provide one example implementation. Other electrodes or electrode combinations can be substituted for those utilized in the exemplary method 1300.

In the flow diagram of FIG. 13, the operations are summarized in individual blocks. Some operations may be performed in hardware and/or as machine-readable instructions (software or firmware) that can be executed by a processor, such as microcontroller 221.

At block 1302, the method 1300 begins by detecting a ventricular tachycardia. For example, the ventricular sensing circuit 246 and arrhythmia detector 234 components of the exemplary stimulation device 100 may detect ventricular tachycardia and signal the tiered ATP controller 238.

At block 1304, ATP is delivered through electrodes typically used for pacing. This is the first tier of the tiered method 1300. For example, a first-tier pacing vector may be established between the RV tip electrode 128 and the RV coil electrode 132. Or the corresponding pacing electrodes could be used in the left ventricle. Both right and left ventricular electrodes can also be used at the same time. This first tier of the exemplary method 1300 provides a least invasive pacing vector, which is utilized first so that if it works, more invasive pacing vectors at higher tiers of the method 1300 can be avoided.

At block 1306, the method 1300 checks to see if the first tier pacing just applied has terminated the ventricular tachycardia. If the ventricular tachycardia still persists, then the method 1300 escalates to a higher tier.

At block 1308, ATP is delivered through a larger electrode area and thus over a greater volume of excitable cardiac tissue. In one implementation, this second-tier pacing vector is established between the LV ring electrode 116 and the RV coil electrode 132. The resulting second-tier pacing vector provides a greater electrical field than at the first tier, and increases the likelihood of the pulse wavefront coupling across excitable cardiac tissue. Thus, a higher percentage of the tissue has the opportunity to be captured electronically or instantly and this increases the chances of converting the ventricular tachycardia to a normal sinus rhythm.

At block 1310, the method 1300 checks to see if the second tier pacing just applied has terminated the ventricular tachycardia. If the ventricular tachycardia still persists, then the method 1300 escalates to a higher tier.

At block 1312, a third tier of ATP is delivered through an even larger electrode area, through different cardiac tissue, and/or through the same cardiac tissue as at the second tier but using a different pacing vector. In one implementation, the third tier of the tiered ATP is applied between the RV coil electrode 132 and the SVC coil electrode 134. The third-tier pacing vector that results from the use of these electrodes provides different vectors from the second tier pacing and different areas of capture in the left ventricle and especially in the right ventricle. Alternatively, the third-tier ATP can be delivered between an LV coil electrode 602 and the SVC coil electrode 134. Or, the third-tier ATP can be delivered between an LV coil electrode 602 and a parallel combination of the RV coil electrode and SVC coil, e.g., by shorting together these two electrodes.

At block 1314, the method 1300 checks to see if the second tier pacing just applied has terminated the ventricular tachycardia. If the ventricular tachycardia still persists, then the method 1300 escalates to a higher tier.

At block 1316, fourth tier ATP is delivered through an even larger electrode area, this time via the case 200 of the exemplary stimulation device 100 and the RV coil electrode 132. This provides a far-field electrode arrangement that can reach a great volume of cardiac tissue, with the tradeoff that the case 200 electrode is outside the heart and likely to inflict pocket stimulation, experienced by the patient as pain or discomfort. To decrease pain and discomfort of this tier of the tiered ATP, pre-pulsing therapy, as described with respect to FIG. 12, can be applied with the fourth tier ATP.

Alternatively, fourth-tier ATP can be delivered between a parallel combination of the SVC coil electrode 134 and the case 200 (e.g., these two electrodes shorted together) with the RV coil electrode 132 as the other electrode. The resulting fourth-tier pacing vector provides a homogeneous field coverage of the entire left ventricle, which can be successful at converting some difficult ventricular tachycardias.

At block 1318, the method 1300 checks to see if the fourth tier pacing just applied has terminated the ventricular tachycardia. If the ventricular tachycardia still persists, then the method 1300 escalates to a higher tier.

At block 1320, if the ventricular tachycardia has still not been terminated, then one or more cardioversion shocks are applied. Although in one implementation the cardioversion shocks are envisioned as the final tier of the exemplary tiered ATP, some implementations may include more tiers of the exemplary tiered ATP to try before applying cardioversion shocks, or may include tiered variations of the cardioversion shocks.

CONCLUSION

Although exemplary systems and methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method, comprising:
   detecting a ventricular tachycardia; and
   applying a tiered antitachycardia pacing (ATP) therapy consisting of one or more of:
   providing ATP through electrodes of progressively larger surface area,
   providing ATP through progressively larger volumes of cardiac tissue, or
   providing ATP through different pacing vectors.

2. The method as recited in claim 1, further comprising checking whether the ventricular tachycardia has been terminated after each tier of the tiered ATP therapy.

3. The method as recited in claim 1, further comprising applying a pre-pulsing therapy with the tiered ATP therapy.

4. The method as recited in claim 1, wherein applying the tiered ATP therapy includes applying a first tier of the ATP via pacing electrodes.

5. The method as recited in claim 1, wherein providing ATP through different pacing vectors includes providing ATP in a progressive sequence through different pacing vectors, including a vector that uses at least one electrode situated over an epicardium of the heart.

6. The method as recited in claim 1, wherein providing ATP through different pacing vectors includes providing ATP in a progressive sequence through different pacing vectors, including a vector that uses multiple pacing electrodes in combination as a large area electrode.

7. The method as recited in claim 1, wherein providing ATP through different pacing vectors includes providing ATP in a progressive sequence through different pacing vectors, including a vector that uses one or more coronary sinus coil electrodes.

8. The method as recited in claim 1, wherein applying the tiered ATP therapy includes calculating a pulse train for at least some of the tiers of the tiered ATP therapy.

9. The method as recited in claim 1, wherein the pre-pulsing therapy is added to the ATP each time an electrode external to the heart is used to deliver a tier of the tiered ATP.

10. A method, comprising:
    applying antitachycardia pacing to treat ventricular tachycardia;
    sensing whether the ventricular tachycardia has stopped; and
    changing electrode locations to obtain larger electrode surface areas for applying the antitachycardia pacing if the ventricular tachycardia has not stopped.

11. The method as recited in claim 10, further comprising repeating the sensing and the changing electrode locations until the ventricular tachycardia stops.

12. The method as recited in claim 10, wherein the changing electrode locations to obtain larger electrode surface areas for applying the antitachycardia pacing further includes progressively changing from electrodes inside the heart to electrodes outside the heart.

13. An implantable cardiac therapy system comprising:
    at least one lead comprising a plurality of electrodes defining a plurality of stimulation vectors;
    an implantable cardiac therapy device adapted to be connected to the at least one lead and comprising an antitachycardia pacing module to generate antitachycardia pacing pulses to be delivered via the at least one lead via a selected stimulation vector, wherein the implantable cardiac therapy device further comprises a sensor to sense a ventricular tachycardia and to control the antitachycardia pacing module to generate the antitachycardia pacing pulses, and wherein the implantable cardiac therapy device is operative to change stimulation vectors to obtain larger electrode surface areas if the ventricular tachycardia has not stopped.

* * * * *